United States Patent [19]

Wassen et al.

[11] 4,377,700
[45] Mar. 22, 1983

[54] PROCESS FOR THE PREPARATION OF N-(CYCLOHEXYLTHIO)-PHTHALIMIDE

[75] Inventors: Jürgen Wassen, Leverkusen; Heinrich Königshofen, Bergish-Gladbach, both of Fed. Rep. of Germany

[73] Assignee: Bayer Aktiengesellschaft, Leverkusen, Fed. Rep. of Germany

[21] Appl. No.: 299,667

[22] Filed: Sep. 8, 1981

[30] Foreign Application Priority Data

Sep. 12, 1980 [DE] Fed. Rep. of Germany ....... 3034397

[51] Int. Cl.$^3$ ............................................ C07D 209/48
[52] U.S. Cl. .................................................. 548/475
[58] Field of Search ...................... 260/326 S; 548/475

[56] References Cited

U.S. PATENT DOCUMENTS 3,579,460  5/1971  Kerwood ............................ 252/182
4,219,393  8/1980  Lorii et al. ...................... 260/326 S

FOREIGN PATENT DOCUMENTS 197711  11/1977  U.S.S.R. ......................... 260/326 S

OTHER PUBLICATIONS

O. Ermakov et al., Z. H. Org. Khim. 14, 1202–1204 (1978), (English), Reaction of N-Chlorophthalimide with Disulfides.
M. Behforouz et al., J. Org. Chem. 34, 51–55 (1969), Alkyl and Aryl Sulfenimides.
O. Ermakov et al., Z. H. Org. Khim. 12, 234 (1976), (English), Synthesis of N-Cyclohexyl Thiophthalimide.
Houben-Weyl, Methoden der organischen Chemie, vol, IX, p. 275 et. seq.

*Primary Examiner*—Mary C. Lee
*Assistant Examiner*—M. C. Eakin
*Attorney, Agent, or Firm*—Connolly and Hutz

[57] ABSTRACT

A process for the preparation of N-(cyclohexylthio)-phthalimide by the reaction of phthalimide with cyclohexylsulphenylchloride in the presence of a base, characterized in that an alkali or alkaline earth metal hydroxide is used as the base.

4 Claims, No Drawings

PROCESS FOR THE PREPARATION OF N-(CYCLOHEXYLTHIO)-PHTHALIMIDE

The invention relates to a process for the preparation of N-(cyclohexylthio)-phthalimide by the reaction of cyclohexylsulphenylchloride with phthalimide in the presence of aqueous alkali or alkaline earth solutions.

Several processes for the preparation of N-(cyclohexylthio)-phthalimide are already known. Thus, Sigeru Torii et al. in J. Org. Chem. 44, 1554–57 (1979) describe electrolytic synthesis from phthalimide and dicyclohexyldisulphide. However, this process cannot be carried out industrially.

It is also known from the investigations of O. A. Ermakov et al. in Zh. Org. Khim. 14, 1299–1301 (1978) and Zh. Org. Khim. 12, 237 (1976) that N-(cyclohexylthio)-phthalimide can be produced from N-chlorophthalimide and dicyclohexyldisulphide. However, the yields of 60 and 67% achieved by this process are unsatisfactory.

According to a process in U.S. Pat. No. 3,579,460, phthalimide and a solution of cyclohexylsulphenylchloride are combined in dimethylformamide. An equimolar quantity of a tertiary amine is added thereto, and the reaction product formed is precipitated by addition of water. Disadvantages of this process include the use of dimethylformamide which can only be recovered for reuse with difficulty, the large quantitities of water needed to isolate the N-(cyclohexylthio)-phthalimide from the organic solvent and the removal and recovery of the tertiary amine.

Moreover, it is generally known (Houben-Weyl, Methoden der organischen Chemie, Volume IX, page 275 et seq) that alkylsulphenylchorides decompose very rapidly in water, particularly in aqueous alkalihydroxide.

Also, according to the investigations of M. Behforouz and J. E. Kerwood in J. Org. Chem. 34, 51–55 (1969), N-(cyclohexylthio)-phthalimide is unstable in alkaline solutions and hydrolyses rapidly.

It was therefore surprising that it was possible by the process according to the invention to prepare N-(cyclohexylthio)-phthalimide from phthalimide and cyclohexylsulphenylchloride in an almost quantitative yield by using an aqueous alkali or alkaline earth metal hydroxide solution as base.

The invention therefore provides a process for the preparation of N-(cyclohexylthio)-phthalimide by the reaction of phthalimide and cyclohexylsuphenylchloride in the presence of a base which is characterised in that an aqueous alkali and/or alkaline earth metal hydroxide solution is used as the base.

Alkali or alkaline earth metal hydroxides dissolved or precipitated in water are used as the base. Caustic soda solution, caustic potash solution or calcium hydroxide are preferred. The concentration in water is as desired. The base used acts mainly as a hydrochloric acid acceptor.

For the reaction, water can also be used additionally as reaction medium.

The water, whether added as an extra or used as solvent or dispersant for the base, should be present at least in sufficient quantities to dissolve any alkali or alkaline earth metal chloride formed during the reaction. The maximum quantity is optional in itself. However, it is advisable, for economic reasons, not to add more water than that needed to dissolve the phthalimide salt formed from the phthalimide and base. However, the phthalimide can also be present as a suspension without disadvantage.

Cyclohexylsulphenylchloride can be prepared by several processes, but preferably from cyclohexylmercaptan or dicyclohexyldisulphide and chlorine. The cyclohexylsulphenylchloride can be present in an organic solvent or in solid form.

Emulsifiers which act in alkaline medium can be added to improve the mixing of the aqueous and organic constituents during the reaction.

The phthalimide, cyclohexylsulphenylchloride and the base are preferably reacted in the same molar ratio. The phthalimide and the base can however also be used in a molar excess, based on the sulphenylchloride. If an excess is considered, it is advisable not to exceed 1 to 10 mol %.

In the process according to the invention, the N-(cyclohexylthio)-phthalimide is obtained in a very high yield and in a high purity.

The reaction takes place in accordance with the following reaction scheme

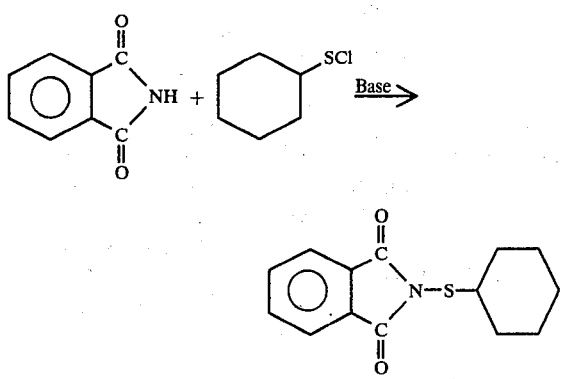

The reaction can be carried out at temperatures of between −10° and 100° C., but temperatures of between 0° and 20° C. are preferably maintained. At temperatures below 0° C., melting-point-reducing substances such as salts and water-soluble solvents may be added.

The compound prepared according to the invention is used for delaying the start of vulcanisation of natural and/or synthetic rubbers. The invention is further illustrated by the following Examples:

EXAMPLE 1

In a stirreer vessel there are placed:

| | |
|---|---|
| 200 | parts by weight water; |
| 29.4 | parts by weight phthalimide; and |
| 0.1 | part by weight emulsifier Erkantol BXG. |

The mixture is cooled to 5° C. The following are then added, with stirring:

| | |
|---|---|
| 18 | parts by weight 45% NaOH; and |
| 30.1 | parts by weight cyclohexylsulphenyl-chloride in |
| 100 | parts by weight pentane. |

After 15 minutes subsequent stirring time, the precipitated solid product is separated from the liquid phases, washed with 20 parts by volume of pentane, and the product is dried.

Yield: 51 parts by weight of N-(cyclohexylthio)-phthalimide ≙ 97.9% of the theoretical yield, based on the phthalimide and cyclohexylsulphenylchloride used.

The yield of pure substance is 98%.

EXAMPLE 2

In a stirrer vessel there are placed:

| |
|---|
| 100 parts by weight water; |
| 29.4 parts by weight phthalimide; and |
| 0.1 part by weight emulsifier Erkantol BXG. |

The mixture is cooled to 5° C. The following are then added, with stirring:

| |
|---|
| 39.4 parts by weight 50% caustic potash solution; |
| 30.1 parts by weight cyclohexylsulphenylchloride in |
| 120 parts by weight hexane. |

After 15 minutes subsequent stirring time, the precipitated solid product is separated from the liquid phases, washed once with 20 parts by volume of hexane and then with water, and the product is dried.

Yield: 50.5 parts by weight of N-(cyclohexylthion)-phthalimide ≙ 96.7% of the theoretical yield, based on the phthalimide and cyclohexylsulphenyl chloride used.

The yield of pure substance is 98%.

EXAMPLE 3

In a stirrer vessel there are placed:

| |
|---|
| 100 parts by weight water; |
| 29.4 parts by weight phthalimide; and |
| 0.1 part by weight emulsifier Erkantol BXG |

The mixture is cooled to 10° C. The following are then added with stirring:

| |
|---|
| 130 parts by weight 10% milk of lime; and |
| 30.1 parts by weight cyclohexylsulphenyl-chloride in |
| 400 parts by weight toluene. |

After 15 minutes subsequent stirring time, the two phases are separated, the organic material is dried and concentrated to a tenth part. 100 parts by weight of pentane are added thereto and the solid product is separated and dried.

Yield: 50 parts by weight of N-(cyclohexylthio)-phthalimide ≙ 95.8% of the theoretical yield, based on the phthalimide and cyclohexylsulphenylchloride used.

The yield of pure substance is 99%.

We claim:

1. In the process of preparing N-(cyclohexylthio)-phthalimide by the reaction of one mol of phthalimide with one mol of cyclohexylsulphenylchloride in the presence of a base, the improvement which comprises employing an aqueous solution of alkali metal hydroxide or alkaline earth metal hydroxide as the base in an amount which supplies at least one mol of said base and up to a 10 mol % excess of said base, based on cyclohexylsulphenylchloride.

2. The process of claim 1 wherein the reaction is carried out at a temperature of from $-10°$ to $100°$ C.

3. The process of claim 1 wherein the reaction is carried out at a temperature of from $0°$ to $20°$ C.

4. The process of claim 1 wherein an emulsifier which acts in alkaline medium is employed.

* * * * *